(12) United States Patent
Chen et al.

(10) Patent No.: US 6,420,144 B1
(45) Date of Patent: Jul. 16, 2002

(54) METHOD FOR AUTOMATED MOLECULAR CLONING

(75) Inventors: Zhidong Chen; Duane E. Ruffner, both of Salt Lake City, UT (US)

(73) Assignee: Salus Therapeutics, Inc., Salt Lake City, UT (US)

(*) Notice: Subject to any disclaimer, the term of this patent is extended or adjusted under 35 U.S.C. 154(b) by 0 days.

(21) Appl. No.: 09/605,566

(22) Filed: Jun. 28, 2000

(51) Int. Cl.[7] .................. C12P 19/34; C07H 21/02; C12Q 1/68
(52) U.S. Cl. .................. 435/91.1; 435/6; 435/91.2; 435/440; 536/23.1; 536/24.3; 536/24.31; 536/24.32; 536/24.33
(58) Field of Search .................. 435/6, 91.1, 91.2, 435/440; 536/23.1, 24.3, 24.31, 24.33

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,889,818 A | 12/1989 | Gelfand et al. |
| 5,279,952 A * | 1/1994 | Wu .................. 435/172.3 |
| 5,506,137 A | 4/1996 | Mathur et al. |
| 5,514,568 A * | 5/1996 | Stemmer .................. 435/91.2 |
| 5,525,493 A * | 6/1996 | Hornes et al. .................. 435/91.2 |
| 5,545,552 A | 8/1996 | Mathur |
| 5,700,672 A | 12/1997 | Mathur et al. |
| 5,942,391 A | 8/1999 | Zhang et al. |
| 6,054,564 A | 4/2000 | Barany et al. |

FOREIGN PATENT DOCUMENTS

WO  WO 99/35281  7/1999

OTHER PUBLICATIONS

Bi et al, "Site–directed mutagenesis by combined chain reaction", Anal. Biochem. 256:137–140 (Feb. 1998).*
Ke et al, "Rapid and efficient site directed mutagenesis by single tube megaprimer PCR method", Nucleic Acids Research 25(16):3371–3372 (1997).*
Ling et al, "Approaches to DNA mutagenesis, an overview", Anal. Biochem. 254:157–178 (1997).*
A. Chien et al., 127 J. Bacteriol. 1550 (1976).
A.S. Kaledin et al., 45 Biokhimiya 494 (1980).
F. Barany, 88 Proc. Nat'l Acad. Sci. USA 189 (1991).
M. Takahashi et al., 259 J. Biol. Chem. 10041–10047 (1984).
M. Schalling et al., 4 Nature Genetics 135 (1993).
G.J. Chen, et al. BioTechniques 28:498–505 (Mar. 2000).

* cited by examiner

Primary Examiner—Jeffrey Fredman
(74) Attorney, Agent, or Firm—Thorpe North & Western, LLP.

(57) ABSTRACT

A method for the automated molecular cloning and amplification of closed circular clones in vitro in a cell-free system using a pair of particularly designed cloning primers in a ligation-during-amplification (LDA) process, in which the fully extended DNA strands containing the donor sequence are ligated by DNA ligase and then used as templates for subsequent amplification. By designing particular cloning primers, the present invention can be used to obtain amplified closed circular nucleic acid clones with inverted or non-inverted insertions or substitutions with a donor nucleic acid fragment, or deletions of a fragment of the closed circular nucleic acid.

20 Claims, 4 Drawing Sheets

SEQUENCE LISTING

<160> NUMBER OF SEQ ID NOS: 8

<210> SEQ ID NO 1
<211> LENGTH: 34
<212> TYPE: DNA
<213> ORGANISM: Artificial Sequence
<220> FEATURE:
<223> OTHER INFORMATION: PCR primer

<400> SEQUENCE: 1 cac cga aac gcg cga gat atc ata tgg tga ccg g          34

<210> SEQ ID NO 2
<211> LENGTH: 34
<212> TYPE: DNA
<213> ORGANISM: Artificial Sequence
<220> FEATURE:
<223> OTHER INFORMATION: PCR primer

<400> SEQUENCE: 2 cga ggc cct ttc gtc gat atc cag aca tga taa g          34

<210> SEQ ID NO 3
<211> LENGTH: 34
<212> TYPE: DNA
<213> ORGANISM: Artificial Sequence
<220> FEATURE:
<223> OTHER INFORMATION: PCR primer

<400> SEQUENCE: 3 cga ggc cct ttc gtc gat atc ata tgg tga ccg g          34

-continued

```
<210> SEQ ID NO 4
<211> LENGTH: 34
<212> TYPE: DNA
<213> ORGANISM: Artificial Sequence
<220> FEATURE:
<223> OTHER INFORMATION: PCR primer

<400> SEQUENCE: 4 cac cga aac gcg cga gat atc cag aca tga taa g                         34

<210> SEQ ID NO 5
<211> LENGTH: 30
<212> TYPE: DNA
<213> ORGANISM: Artificial Sequence
<220> FEATURE:
<223> OTHER INFORMATION: PCR primer

<400> SEQUENCE: 5 gaa tgg cgc ctg atg atg gcc aag ttg acc                               30

<210> SEQ ID NO 6
<211> LENGTH: 30
<212> TYPE: DNA
<213> ORGANISM: Artificial Sequence
<220> FEATURE:
<223> OTHER INFORMATION: PCR primer

<400> SEQUENCE: 6 tcg ggg ctg gct taa tca gtc ctg ctc ctc                               30

<210> SEQ ID NO 7
<211> LENGTH: 33
<212> TYPE: DNA
<213> ORGANISM: Artificial Sequence
<220> FEATURE:
<223> OTHER INFORMATION: PCR primer

<400> SEQUENCE: 7 gaa tgg cgc ctg atg tga tta agc cag ccc cga                           33

<210> SEQ ID NO 8
<211> LENGTH: 33
<212> TYPE: DNA
<213> ORGANISM: Artificial Sequence
<220> FEATURE:
<223> OTHER INFORMATION: PCR primer

<400> SEQUENCE: 8 tcg ggg ctg gct taa act cat cag gcg cca ttc                           33
```

METHOD FOR AUTOMATED MOLECULAR CLONING

BACKGROUND OF THE INVENTION

This invention relates to a method for automated in vitro molecular cloning and amplification. More particularly, the invention relates to a process for the cell-free automated molecular cloning of a donor DNA which has been inserted into any nucleotide position in a recipient DNA, and amplifying the recombinant closed circular DNA clone in a single process.

Conventional methods for molecular cloning require multiple separate processes: first, donor and recipient DNA have to be digested by the proper restrictive enzymes; the digested DNA fragments have to be isolated and then subjected to a ligation process in order to insert the donor DNA into the recipient DNA; the resulting donor-recipient DNA is then used to transform the proper host cell to be able to amplify the recombinant donor-recipient DNA; and finally a selection process is performed to select the desired molecular clone with the correct insertion orientation. These conventional methods typically require several days to weeks of labor intensive manipulation in order to obtain and identify the desired molecular clone. Furthermore, cloning by conventional methods is limited by the availability of restriction sites on the recipient and/or donor DNAs. In order to obtain the desired clone, site-directed mutagenesis is often required to introduce restriction sites into the recipient and/or donor DNAs. This also makes the cloning process very labor-intensive and time-consuming.

Polymerase chain reaction (PCR) is a powerful method for the rapid and exponential amplification of target nucleic acids. E.g., U.S. Pat. Nos. 4,683,195 and 4,683,202, hereby incorporated by reference. PCR has facilitated the development of gene characterization and molecular cloning technologies including direct sequencing of PCR-amplified DNA, the determination of allelic variation, and the detection of infectious and genetic disorders. PCR is performed by repeated cycles of heat denaturation of a DNA template containing the target sequence, annealing of opposing primers to the complementary DNA strands, and extension of the annealed primers with a DNA polymerase. Multiple PCR cycles result in the exponential amplification of the nucleotide sequence delineated by the flanking amplification primers.

An important modification of the original PCR technique is the incorporation of a thermostable DNA polymerase into the PCR protocol which obviates the need for repeated enzyme additions and permits elevated annealing and primer extension temperatures, this enhances the specificity of the primer/template association. Several thermostable DNA polymerases have also been discovered and commercialized, such as the thermostable DNA polymerase from *Pyrococcus furiosus* (Pfu DNA polymerase; U.S. Pat. No. 5,545,552, hereby incorporated by reference), the thermostable DNA polymerase from Thermus flavus (Tfl DNA polymerase; Epicentre Technologies), the thermostable DNA polymerase from *Thermus thermophilus* (Tth DNA polymerase, Epicentre Technologies, Madison, Wis.), a mixture of Taq DNA polymerase and Pyrococcus species GB-D thermostable DNA polymerase (ELONGASE™, Life Technologies, Inc., Gaithersburg, Md.), the thermostable DNA polymerase from *Thermococcus litoralis* (Vent$_R$® DNA polymerase, New England Biolabs, Beverly, Mass.), and AMPLITHERM™ DNA polymerase (proprietary thermostable DNA polymerase, Epicentre Technologies). Thermostable DNA polymerases thus serve to increase the specificity and simplicity of PCR.

Another type of cloning method is the so-called "ligation independent cloning" in which a PCR product is produced, purified, denatured along with a recipient DNA, which is then subsequently hybridized to the recipient DNA and results in a nicked or linear recombinant DNA molecule. Because the resulting recombinant molecules are not in a closed circular form they have to be introduced into the proper host cell in order to allow the repair mechanism of the host cell to produce the closed circular recombinant DNA molecule to allow for it to be amplified. Therefore, the cloning efficincy of this method is several orders of magnitude lower than other conventional cloning methods.

As discussed above conventional cloning methods are relatively complex procedures that suffer from drawbacks that make them not amenable to automation. They are labor-intensive and time-consuming. Therefore, a method for automated molecular cloning and amplification of a closed circular recombinant DNA in a single process is desired and provides for a significant advancement in the art.

BRIEF SUMMARY OF THE INVENTION

The present invention provides a method of in vitro automated molecular cloning of a selected donor DNA that has been inserted into a closed circular recipient DNA.

The invention also provides a method of in vitro automated molecular cloning of a selected segment DNA that has been deleted from a closed circular recipient DNA.

The invention further provides a method of in vitro automated molecular cloning of a selected donor DNA that substitutes for a selected segment of a closed circular recipient DNA.

The method for the in vitro automated molecular cloning and amplification of a closed circular nucleic acid comprising:
(a) mixing an effective amount of a donor nucleic acid, a recipient nucleic acid, a pair of 5'-phosphorylated cloning primers, a thermostable DNA ligase, a thermostable DNA polymerase, all four deoxyribonucleoside triphosphates, and an appropriate buffer comprising any cofactor required for activities of both the ligase and polymerase, to result in a cloning mixture; and
(b) thermocycling said cloning mixture through a selected number of cycles at:
(i) a temperature suitable for denaturing the nucleic acids,
(ii) a temperature suitable for annealing the cloning primers to the denatured donor nucleic acid,
(iii) a temperature suitable for polymerase-catalyzed extension of the cloning primers,
(iv) repeating (i) to (iii) to form a pair of insertion primers containing the donor nucleic acid to be inserted,
(v) a temperature suitable for denaturing the nucleic acids,
(vi) a temperature suitable for annealing the insertion primers to the denatured recipient nucleic acid, and
(vii) a temperature suitable for ligase-catalyzed closing of the extended insertion primers, which results in an amplified closed circular nucleic acid recombinant clone containing the donor nucleic acid.

In one illustrative embodiment of the invention, the temperature suitable for polymerase-catalyzed extension of the primers is the same as the temperature suitable for ligase-catalyzed closing of the extended primers. The temperature suitable for annealing the primers to the denatured template can also be the same as the temperature suitable for polymerase-catalyzed extension of the primers.

In preferred embodiments, the cloning mixture is held at the temperature suitable for denaturing the template for about 1 second to 2 minutes in each cycle; the cloning mixture is held at the temperature suitable for annealing the primers to the denatured template for about 1 second to 5 minutes in each cycle; and the cloning mixture is held at the temperature suitable for polymerase-catalyzed extension of the primers and ligase-catalyzed closing of the extended primers for about 1 to 20 minutes in each cycle.

By designing particular cloning primers, the present invention can be used to obtain amplified closed circular nucleic acid clones with inverted or non-inverted insertions or substitutions with a donor nucleic acid fragment, or a deletion of a fragment of the closed circular nucleic acid. When the 3' and 5' portions of the pair of cloning primers are complementary to different strands(+/− or −/+) of the donor and recipient DNA, the resulting amplified closed circular clone comprises a donor sequence inserted in an inverted orientation. When the 3' and 5' portions of the pair of cloning primers are complementary to the same strands(+/+ or −/−) of the donor and recipient DNA, the resulting amplified closed circular clone comprises a donor sequence inserted in a non-inverted orientation. When the 3' portions of the cloning primers are complementary to the donor DNA and 5' portions of the cloning primers are complementary to sequences flanking a region to be substituted on recipient DNA, the resulting amplified closed circular clone comprises the substituted recipient DNA with the donor DNA. When the cloning primers are complementary to sequences flanking a region to be deleted on the recipient DNA, the amplified closed circular clone has that region deleted.

Other features and advantages of the invention will become apparent from the following detailed description, taken in conjunction with the accompanying drawings, which illustrate, by way of example, the features of the invention.

DETAILED DESCRIPTION

Before the present method for automated molecular cloning and amplifying closed circular clones in vitro in a cell-free system is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a reaction mixture containing "a thermostable DNA ligase" includes a mixture of two or more of such thermostable ligases, reference to "a thermostable DNA polymerase" includes reference to one or more of such polymerases, and reference to "a template" includes reference to a mixture of two or more templates.

In describing and claiming the present invention, the following terminology will be used in accordance with the definitions set out herein.

As used herein, "ligation-during-amplification," "LDA," and similar terms mean a process comprising use of a thermostable DNA ligase in a PCR reaction under conditions that permit the production and amplification of closed circular DNA. That is, the reaction conditions permit both the extension of the primers and the ligation of adjacent 5'-phosphate groups and 3'-hydroxyl groups to form phosphodiester bonds, thus closing the synthesized DNA to form a closed circular DNA. It will be recognized by a person of ordinary skill in the art that the 5'-phosphate groups will ordinarily be provided from 5'-phosphorylated primers. As is well known in the art, these 5'-phosphate groups can be added to a primer by a reaction catalyzed by T4 polynucleotide kinase, or be added at the time of primer synthesis. A more detailed description of LDA is disclosed in the copending patent application PCT/US99/00455 filed Jan. 9, 1999, hereby fully incorporated by reference.

As used herein, "polymerase chain reaction" or "PCR" means a process such as is described in U.S. Pat. Nos. 4,683,195 and 4,683,202 for the amplification of a linear segment of DNA using at least two primers and a DNA polymerase. As currently practiced, such a polymerase would be a thermostable enzyme.

As used herein, "cloning primers" means a pair of synthetic nucleic acid sequences having particular complementary characters according to the particular clone desired. When the 3' and 5' portions of the pair of cloning primers are complementary to different strands(+/− or −/+) of the donor and recipient DNA, the resulting amplified closed circular clone comprises a donor sequence inserted in an inverted orientation. When the 3' and 5' portions of the pair of cloning primers are complementary to same strands(+/+ or −/−) of the donor and recipient DNA, the resulting amplified closed circular clone comprises a donor sequence inserted in a non-inverted orientation. When the 3' portions of the cloning primers are complementary to the donor DNA and 5' portions of the cloning primers are complementary to sequences flanking a region to be substituted on the recipient DNA, the resulting amplified closed circular clone comprises the substituted recipient DNA with the donor DNA. When the cloning primers are complementary to sequences flanking a region to be deleted on the recipient DNA, the amplified closed circular clone has that region deleted. In this case, the cloning primers also refers to "deletion primers".

As used herein, "cloning reaction mixture" means a mixture suitable for carrying out PCR, containing a pair of cloning primers such that the 3' portion of the primers are complementary to the donor nucleic acid and the 5' portion of the primers are complementary to the recipient nucleic acid, a suitable amount of a thermostable DNA polymerase, a template DNA (preferably double-stranded) for being amplified, ATP, suitable amounts of each of the four deoxyribonucleoside triphosphates (dNTPs), and buffers, salts, preservatives, reducing agents, and water as may be required.

As used herein, "thermostable DNA ligase" means any DNA ligase that maintains its activity for ligating DNA after being exposed to a plurality of cycles of thermocycling as would occur in a polymerase chain reaction or PCR. PCR is normally carried out by repeated cycling of the reaction mixture between temperature conditions suitable for melting or denaturation of double-stranded template DNA (usually about 95° C.), annealing of primers to the melted (i.e. single-stranded) template DNA (usually about 50° C.), and elongating the annealed primers by primer extension (usually about 72° C.). The thermostable DNA polymerases typically used in PCR survive these cycles of temperature change. For example, *Thermus aquaticus* DNA polymerase (Taq DNA polymerase) is a thermostable enzyme that replicates DNA at 74° C., A. Chien et al., 127 J. Bacteriol. 1550 (1976); A. S. Kaledin et al., 45 Biokhimiya 494 (1980), and remains functional even after incubation at 95° C. For example, U.S. Pat. No. 4,889,818, hereby incorporated by reference, describes a purified thermostable DNA polymerase isolated from *Thermus aquaticus*. Thermostable DNA ligases are also well known in the art and are commercially available. For example, a thermostable DNA ligase from *Pyrococcus furiosus* (Pfu DNA ligase; U.S. Pat. Nos. 5,506,137 and 5,700,672, hereby incorporated by reference) is available from Stratagene (La Jolla, Calif.). This enzyme catalyzes the linkage of adjacent 5'-phosphate and 3'-hydroxy ends of double-stranded DNA at about 45° C. to 80° C. The enzyme is highly thermostable, having a half-life of greater than 60 minutes at 95° C. The temperature optimum for nick-sealing reactions is about 70° C. with this enzyme. By way of further example, Taq DNA ligase (from *Thermus aquaticus*) catalyzes the formation of a phosphodiester bond between juxtaposed 5'-phosphate and 3'-hydroxyl termini of two adjacent oligonucleotides that are hybrized to a complementary DNA. Taq DNA ligase is active at elevated temperatures (45° C. to 65° C.). F. Barany, 88 Proc. Nat'l Acad. Sci. USA 189 (1991); M. Takahashi et al., 259 J. Biol. Chem. 10041–10047 (1984). By way of still a further example, AMPLIGASE® thermostable DNA ligase (Epicentre Technologies) catalyzes the NAD-dependent ligation of adjacent 5'-phosphorylated and 3'-hydroxylated termini in duplex DNA structures. This enzyme has a half-life of 48 hours at 65° C. and greater than 1 hour at 95° C. This thermostable DNA ligase has also been shown to be active for at least 500 thermal cycles (94° C./80° C.) or 16 hours of cycling. M. Schalling et al., 4 Nature Genetics 135 (1993).

It is recognized that many enzymes including polymerases and ligases require cofactors for activity. For example, Taq DNA ligase requires $NAD^+$ as a cofactor. Therefore, a reaction catalyzed by Taq DNA ligase will require that an appropriate amount of $NAD^+$ be added to the reaction mixture.

As used herein, "temperature suitable for denaturing the template" means the temperature at which the template is melted or denatured in light of conditions present in the reaction mixture know to affect the melting of nucleic acids, such as strandedness, monovalent cation concentration, GC content, length of the nucleic acid, presence or absence of mismatches, and the concentration of certain solvents that affect melting. These factors are well known in the art, as are empirical formulas for determining the thermal melting temperatures that occur under selected conditions. A temperature above the thermal melting temperature ($T_m$) of the template will be selected. Denaturation temperatures of about 95° C. are typical.

As used herein, "temperature suitable for annealing the primers to the denatured template" means the temperature at which the single-stranded primers will anneal, by hybridization, to the denatured (single-stranded) template nucleic acid. The same factors that affect denaturation also affect annealing. Since the primers are typically in the range of about 10–30 nucleotide residues in length, as opposed to templates that are usually thousands of nucleotide residues in length, and since the thermal melting temperatures of short nucleic acids are lower than for longer nucleic acids, the annealing temperature will be well below the thermal melting temperature of the template. A temperature of about 40–50° C. is typical.

As used herein, "temperature suitable for polymerase-catalyzed extension of the primers" means a temperature at which the thermostable DNA polymerase is active. Preferably, the temperature is near the temperature optimum of the enzyme. For example, the *Thermococcus litoralis* DNA polymerase is maximally active at about 72–80° C. This is typical of thermostable polymerases.

As used herein, "temperature suitable for ligase-catalyzed closing of the extended primers" means the temperature at which the thermostable DNA ligase is active. Preferably, this temperature is near the temperature optimum of the enzyme and can be the same temperature selected for carrying out the polymerase-catalyzed extension reaction.

One illustrative example of using the automated cloning method of the present invention is to insert a donor DNA sequence into a circular DNA and amplify the closed circular clone in vitro and which comprises the following steps:

(a) mixing the closed circular recipient DNA, either single-stranded or double-stranded, a donor DNA, a pair of 5'phosphorylated cloning primers, deoxyribonucleotides, thermostable DNA polymerase, thermostable DNA ligase, and a reaction buffer that supports the activity of both the polymerase and the ligase, to form a cloning mixture; and (b) subjecting the cloning mixture to thermocycles of denaturation of the DNA at around 95° C., annealing of the cloning primers to the donor DNA at around 50° C., extension of the cloning primer at around 70° C., copying the to-be-cloned DNA to form insertion primers, denaturation of the DNA at around 95° C., annealing of the insertion primers to the recipient DNA at around 50° C., extension of the insertion primers on recipient DNA templates, and ligation of the fully extended strands at around 70° C. to form and eventually amplify the closed circular recombinant molecular clone.

Figure 1:
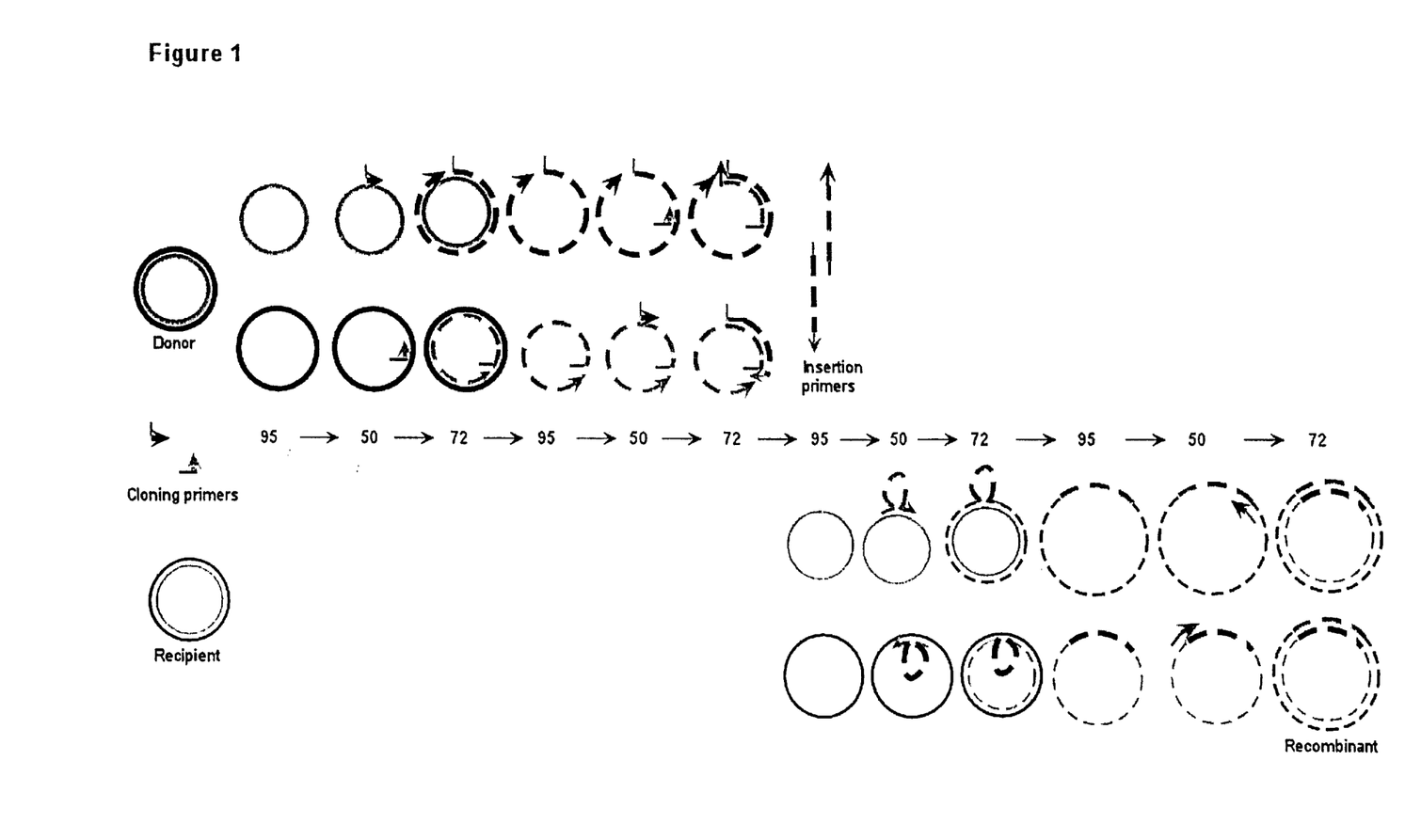
FIG. 1 is a schematic illustration of cloning and amplifying the closed circular clone of a donor sequence being inserted into a recipient nucleic acid in an inverted orientation.

The 3' portion of the cloning primers contain sequences that are complementary to the donor DNA and the 5' portion of the cloning primers also contain sequences that are complementary to the donor DNA. As it is commonly known, synthesis of nucleic acid can only happen in the 5' to 3' direction. Therefore, in the first primer annealing-extension cycle, only the donor DNA can be copied and form insertion primers containing the donor sequences to be inserted. In subsequent annealing-extension cycles, the insertion primers is inserted into the recipient DNA through the complementary of the sequences in the 5' portions of the cloning primers to that of the recipient DNA. This process is illustrated in FIG. 1 and Example 1.

The present invention combines a unique cloning primer design into an LDA procedure for molecular cloning in a single automated reaction. By designing particular cloning primers, the present invention can be used to obtain amplified closed circular nucleic acid clones with inverted or non-inverted insertions or substitutions with a donor nucleic acid fragment, or deletions of a fragment of the closed circular nucleic acid at any one or multiple nucleotide position(s) in the recipient DNA.

Conventional methods for molecular cloning require multiple and labor intensive processes such as restriction enzyme digestion, purification, transformation and selection. LDA-mediated automated molecular cloning does not require these processes, and the clone is amplified directly in the automated LDA cycles. Therefore, it is a much simpler, easier, and faster method for molecular cloning.

Since many modifications, variations and changes in detail can be made to the described preferred embodiment of the invention, it is intended that all matters in the foregoing description and the following examples are interpreted to illustrate and not in any way to limit the invention.

EXAMPLE 1

To demonstrate the successful use of the automated molecular cloning method of this invention, a bleomycin resistance gene from plasmid pUT626 is cloned into plasmid pUC19 in an inverted orientation in order to obtain the new plasmid pUCiBle, using the procedure of this invention.

The pUT626 contains a bleomycin resistance gene, the pUC19 possesses an ampicillin resistance gene and a lacZ' gene. Since the cloned pUCiBle contains all three genes, only pUCiBle transformed bacteria can grow up on medium containing the antibiotics bleomycin and ampicillin and form blue colonies on X-gal containing agar plates.

First, a pair of cloning primers having the following nucleotide sequences were designed and synthesized.
Primer 19(−)626(+):
5P-CAC CGA AAC GCG CGA GAT ATc ata tgg tga ccg g-3'
Primer 19(+)626(−):
5'P-CGA GGC CCT TTC GTC GAT ATc cag aca tga taa g-3'

These primers are 5' phosphorylated to allow ligation of the nick in the newly synthesized DNA strand by the thermostable DNA ligase. The sequences in lowercase at the 3' portions of the primers are complementary to the donor DNA pUT626. Primers 19(−)626(+) and 19(+)626(−) anneal to nucleotides 1–14 in the outer strand and 1012–1025 in the inner strand of pUT626 respectively(FIG. 1). The sequence from nucleotide position 1 to 1025 in pUT626 contains the bleomycin resistance gene and its promoter. The sequences in italics at the 5' portions of the primers are complementary to the recipient DNA pUC19. Primers 19(−)626(+) and 19(+)626(−) anneal to nucleotides −15 in the inner strand and 2672–2686 in the outer strand of pUC19 respectively. This primer design allows the bleomycin resistance gene to be inserted into nucleotide position 1 in pUC19 in an inverted orientation. The bold GATATc sequence is an artificially introduced restriction site to facilitate the removal of the inserted DNA in pUCiBle by the restriction enzyme EcoRV.

As illustrated in FIG. 1, thick and thin lines represent donor and recipient sequences respectively, black and gray lines represent sequences of the inner and outer strands respectively. The cloning primers are shown as tailed arrows, their heads (3') and tails (5') are complementary to the donor and recipient respectively. Note that the head and tail of the same primer have different colors. Dashed lines indicate newly synthesized strands.

Second, the following reagents were mixed in a 0.5-ml thin wall PCR tube: 0.5 µl of 0.1 µg/µl pUT626, 0.5 µl of 0.1 µg/µl pUC19, 2 µl of 8 µM 19(−)626(+), 2 µl of 8 µM 19(+)626(−), 5 µl of 10×Optibuffer (Bioline, Inc., Las Vegas, Nev.), 2 µl of 50 mM $MgCl_2$, 1 µl of 10 mM dNTPs, 0.5 µl of 10 mM ATP, 1 µl of 4 U/µl Bio-X-Act DNA polymerase (Bioline, Inc., Las Vegas, Nev.), 1 µl of 4 U/µl pfu DNA ligase (Stratagene, La Jolla, Calif.), and 33 µl of deionized water.

The PCR tube containing the cloning mixture was placed in an automated thermocycler (MJ Research, Inc., Watertown, Mass.) and subjected to the following thermocycles: 95° C. 10 sec, 50° C. 30 sec, for 60 cycles. DNA is denatured at 95° C., the cloning primers anneal to the donor (shown) and recipient (not shown) DNA at 50° C. via their 3' and 5' complementary ends respectively. The polymerase extends the primers that anneal to the donor at 72° C. Cloning primers that anneal to the recipient via their 5' complementary ends cannot be extended. As the temperature returns to 95 and then 50° C., the cloning primers can now anneal to the newly synthesized DNA strands. At 72° C., the cloning primers are extended by DNA polymerase copying of the sequence to be cloned which forms the insertion primers, which can be exponentially amplified by the cloning primers in subsequent thermocycles (not shown). DNA is denatured again at 95° C. and as the temperature drops to 50° C. the newly synthesized insertion primers can anneal to the recipient DNA via its 3' and 5' complementary ends thus forming a loop at its center. The loop contains the to be cloned donor sequence. Subsequently, at 72° C., the insertion primers are fully extended on the recipient templates and the nicks are closed by the ligase thereby forming the recombinant DNA. During subsequent thermocycles, the cloning primers and the insertion primers will exponentially amplify the recombinant DNA. As shown, the cloned donor sequence has been inverted in the resulting recombinant.

After the thermocycling, DNA in the reaction mixture was precipitated by ethanol and subsequently digested with the restriction enzyme DpnI, which cuts methylated DNA but not the newly synthesized and unmethylated pUCiBle which destroys the input DNA, i.e., pUT626 and pUC19.

The DpnI treated product was introduced into *E. coli* strain DH5α by electroporation. The transformed bacteria were plated on agar plates containing 20 µg/ml Zeocin (a bleomycin analog), 100 µg/ml ampicillin, and 40 µg/ml X-Gal. The plates were incubated at 37° C. for 16 hours. Approximately 168,000 bacterial colonies were obtained from one thermocycling reaction under the conditions described. These bacterial colonies survived both Zeocin and ampicillin, and showed a blue phenotype, indicating the bleomycin resistance gene had been cloned into the pUC19.

Finally, the plasmid was retrieved from the bacterial colonies for characterization. The bleomycin resistance gene is indeed inserted in the expected nucleotide position and orientation as confirmed by restriction mapping and DNA sequencing.

EXAMPLE 2

Figure 2:
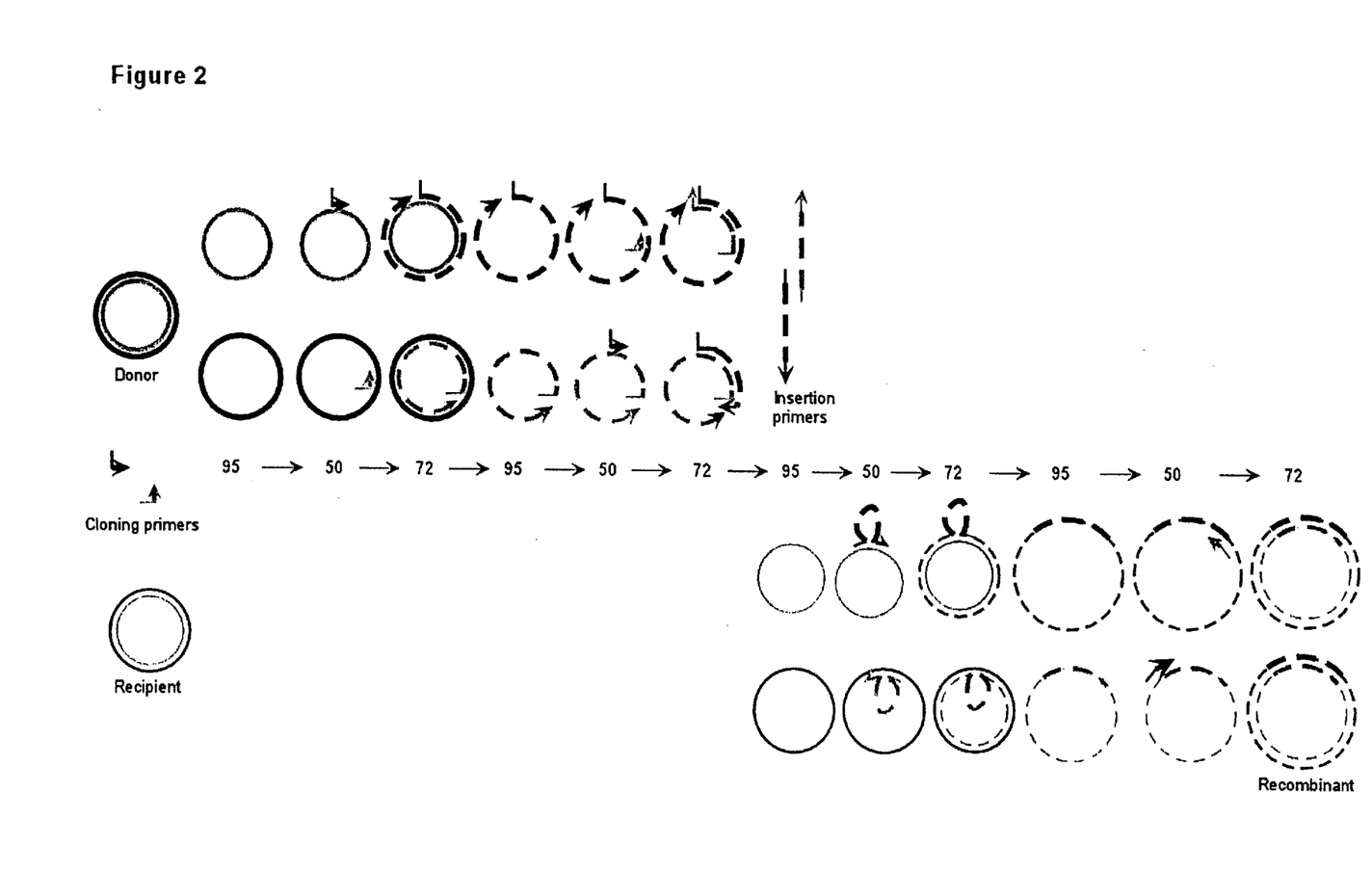
FIG. 2 is a schematic illustration of cloning and amplifying the closed circular clone of a donor sequence being inserted into a recipient nucleic acid in a non-inverted orientation.

This example illustrates cloning a donor sequence into a recipient without inverting the orientation of the insert by making the 3' and 5' portions of each cloning primer complementary to the same strands (inner/inner or outer/outer) of the donor and recipient DNA, respectively (FIG. 2).

In this Example, the bleomycin resistance gene from plasmid pUT626 is cloned into plasmid pUC19 without inverting its orientation so as to obtain the new plasmid pUCble, using the method according to the present invention.

The cloning primers have the following nucleotide sequences:
Primer 19(+)626(+):
5'P- CGA GGC CCT TTC GTC GAT ATc ata tgg tga ccg g-3'
Primer 19(−)626(−):
5'P- CAC CGA AAC GCG CGA GAT ATc cag aca tga taa g-3'

The sequences in lowercase at the 3' portions of the primers are complementary to the donor DNA pUT626. Primers 19(+)626(+) and 19(−)626(−) anneal to nucleotides 1–14 in the outer strand and 1012–1025 in the inner strand of pUT626 respectively (FIG. 2). The sequence from nucleotide position 1 to 1025 in pUT626 contains the bleomycin resistance gene and its promoter. The sequences in italics at the 5' portions of the primers are complementary to the recipient DNA pUC19. Primers 19(−)626(−) and 19(+)626(+) anneal to nucleotides 1–15 in the inner strand and 2672–2686 in the outer strand of pUC19 respectively. This primer design allows the bleomycin resistance gene to be inserted into nucleotide position 1 in pUC19 without inverting its orientation. The bold GATATc sequence is an artificially introduced restriction site to facilitate the removal of the inserted DNA in pUCble by the restriction enzyme EcoRV.

As illustrated in FIG. 2, thick and thin lines represent donor and recipient sequences respectively. Black and gray lines represent sequences of the inner and outer strands respectively. The cloning primers are shown as tailed arrows, their heads (3') and tails (5') are complementary to the donor and recipient respectively. Note that the head and tail of the same primer have the same colors. Dashed lines indicate newly synthesized strands. Donor DNA, recipient DNA, cloning primers, thermostable DNA polymerase, ligase, dNTPs, and buffer are mixed; and the mixture is subjected to thermocycling of 95° C. to 50° C. to 72° C. DNA is denatured at 95° C., the cloning primers anneal to the donor (shown) and recipient (not shown) DNA at 50° C. via their 3' and 5' complementary ends respectively. The polymerase extends the primers that anneal to the donor at 72° C. Cloning primers that anneal to the recipient via their 5' complementary ends cannot be extended. As the temperature returns to 95 and then 50° C., the cloning primers can now anneal to the newly synthesized DNA strands. At 72° C., the cloning primers are extended by DNA polymerase copying of the sequence to be cloned which forms the insertion primers, which can be exponentially amplified by the cloning primers in subsequent thermocycles (not shown). DNA is denatured again at 95° C. and as the temperature drops to 50° C. the newly synthesized insertion primers can anneal to the recipient DNA via its 3' and 5' complementary ends thus forming a loop at its center. The loop contains the to be cloned donor sequence. Subsequently at 72° C., the insertion primers are fully extended on the recipient templates and the nicks are closed by the ligase thereby forming the recombinant DNA. During subsequent thermocycles, the cloning primers and the insertion primers will amplify the recombinant DNA exponentially. As shown, the cloned donor sequence retains its original orientation in the resulting recombinant. The detailed cloning procedures and conditions are the same as described in Example 1.

EXAMPLE 3

Figure 3:
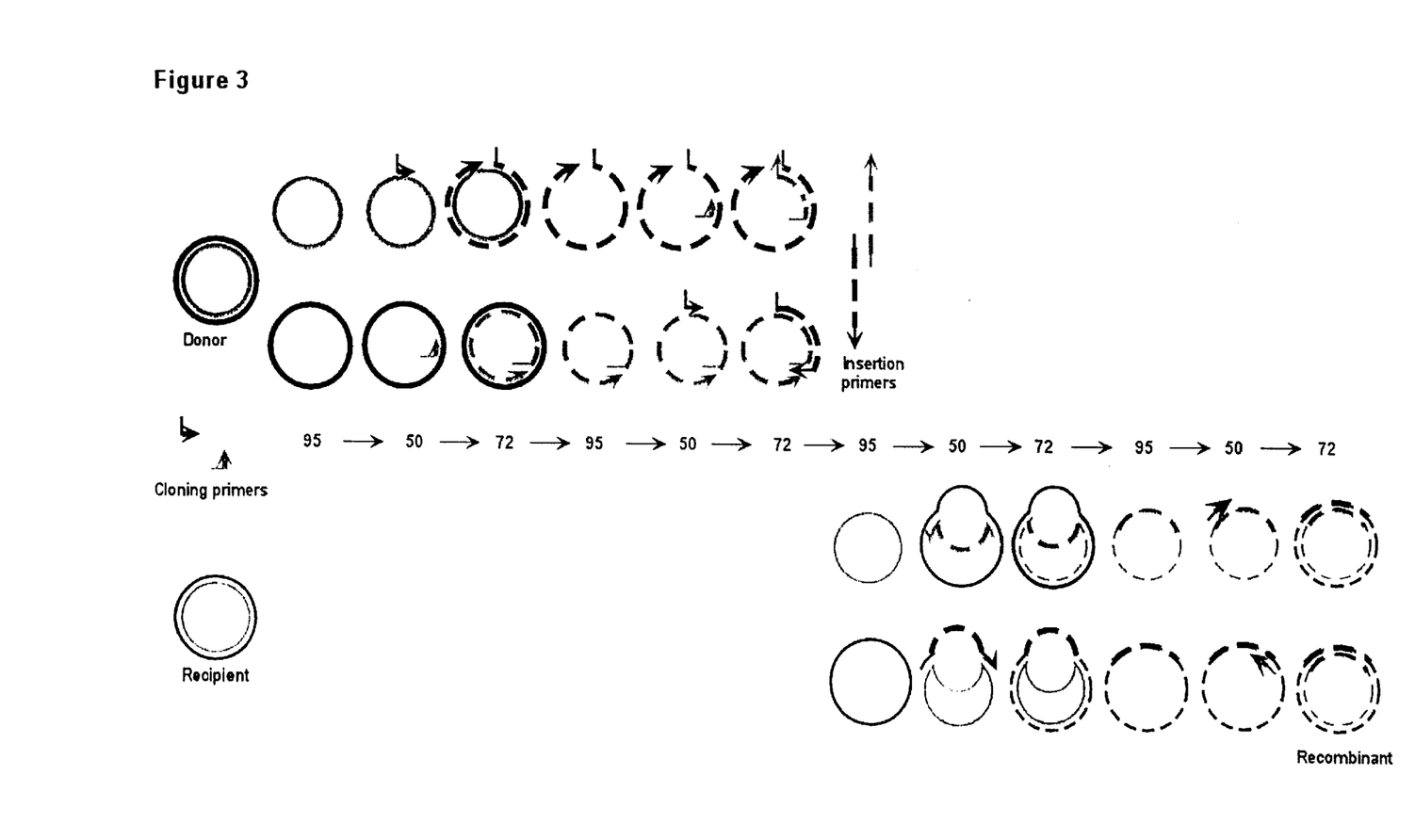
FIG. 3 is a schematic illustration of cloning and amplifying the closed circular clone of a recipient sequence being substituted with a donor sequence.

This example illustrates using the present invention to substitute a sequence, such as a gene, in a circular recipient DNA with a sequence from another circular or linear donor DNA. This is accomplished by using cloning primers complementary to sequences flanking the region to be substituted (FIG. 3). Sequence substitution by the invented method is particularly useful for generating fusion genes, which require accurate in-frame fusion of the two genes.

In this Example, the coding sequence of bleomycin resistance genes from plasmid pUT626 is fused in-frame to the 3' end of the lacZ' gene in plasmid pUC19 to obtain the new recombinant placZ'::ble, using the present procedure. This fusion results from the substitution of the 84 base pairs at the 3' end of the lacZ' gene with the coding sequence (372 base pairs) of the bleomycin resistance gene. The fusion protein lacZ'::ble will render the transformed bacteria resistant to bleomycin and they will have a blue phenotype.

The cloning primers have the following nucleotide sequences:
Primer lac(+)ble(+):
5'P- GAA TGG CGC CTG ATG atg gcc aag ttg acc -3'
Primer lac(−)ble(−):
5'P- TCG GGG CTG GCT TAA tca gtc ctg ctc ctc -3'

The sequences in lowercase at the 3' portions of the primers are complementary to the donor DNA pUT626. Primers lac(+)ble(+) and lac(−)ble(−) anneal to the 5' 15 nucleotides in the outer and inner strands of the 372 base pairs coding sequence of the bleomycin resistance gene, respectively. The sequences in italics at the 5' portions of the primers are complementary to the recipient DNA pUC19. Primers lac(−)ble(−) and lac(+)ble(+) anneal to the 5' 15 nucleotides in the inner and outer strands flanking the 84 base pairs to be substituted in the lacZ' sequence. This primer design allows the bleomycin resistance gene to fuse in-frame with the lacZ' gene at its 3' end.

This substitution event is schematically illustrated in FIG. 3. As illustrated in FIG. 3, the thick and thin lines represent donor and recipient sequences respectively. The black and gray lines represent sequences of the inner and outer strands respectively. The cloning primers are shown as tailed arrows, their heads (3') and tails (5') are complementary to the donor and recipient respectively. Dashed lines indicate newly synthesized strands. Donor DNA, recipient DNA, cloning primers, thermostable DNA polymerase, ligase, dNTPs, and buffer are mixed; and the mixture is subjected to thermocycling of 95° C. to 50° C. to 72° C. DNA is denatured at 95° C., the cloning primers anneal to the donor (shown) and recipient (not shown) DNA at 50° C. via their 3' and 5' complementary respectively. The polymerase extends the primers that anneal to the donor at 72° C. Cloning primers that anneal to the recipient via their 5' complementary cannot be extended. As the temperature returns to 95 and then 50° C., the cloning primers can now anneal to the newly synthesized DNA strands. At 72° C., the cloning primers are extended by DNA polymerase copying of the sequence to be cloned to form the insertion primers, which can be exponentially amplified by the cloning primers in subsequent thermocycles (not shown). DNA is denatured again at 95° C. and as the temperature drops to 50° C., the newly synthesized insertion primers can anneal to the recipient DNA via their 3' and 5' complementary ends. Subsequently at 72° C., the insertion primers are fully extended on the recipient templates and the nicks are closed by the ligase thereby forming the DNA recombinant. During subsequent thermocycles, the cloning primers and the insertion primers will amplify the recombinant DNA exponentially. As shown, the cloned donor sequence (thick line) has replaced the corresponding recipient sequence in the resulting recombinant. The detailed cloning procedures and conditions are the same as described in Example 1.

EXAMPLE 4

Figure 4:
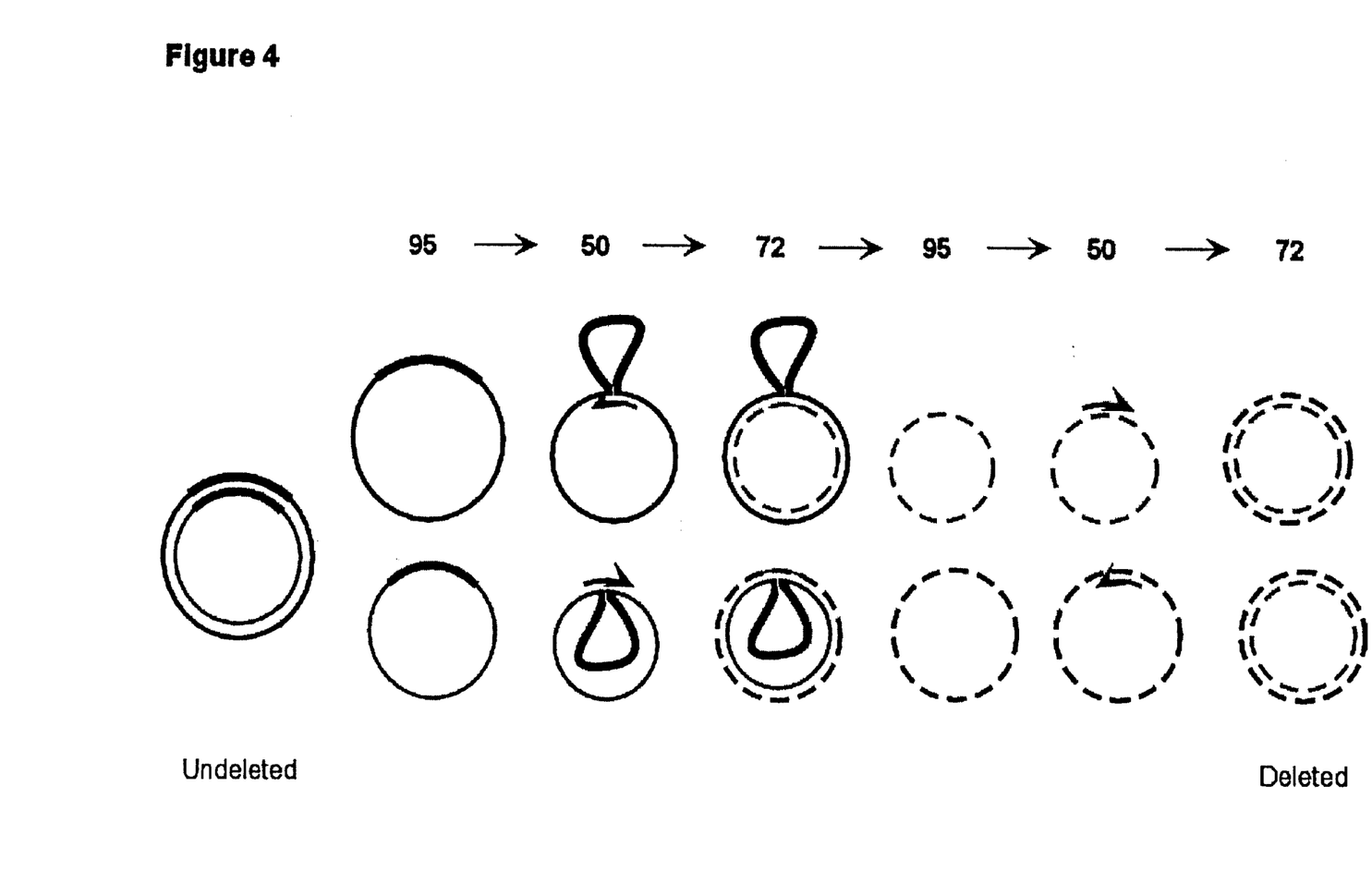
FIG. 4 is a schematic illustration of cloning and amplifying the closed circular clone with a particular region being deleted.

In Example 3, it is demonstrated that the sequence in a recipient DNA can be substituted with a donor sequence by way of a pair of PCR generated insertion primers that contain the donor sequence. If similar insertion primers are synthesized chemically and the primers do not contain a donor sequence, they can be used in the present method to delete a sequence from any circular DNA and amplify the resulting deleted closed circular recombinant DNA exponentially (FIG. 4). These synthetic insertion primers may be termed deletion primers.

In this Example, the 3' 84 nucleotides of the lacZ' gene in plasmid pUC19 is deleted using the invented method. The activity of the shorten lacZ' protein is studied. Two deletion primers are made. The primers have the following sequences.
Primer lacΔ(+):
5'P- GAA TGG CGC CTG ATG TGA tta agc cag ccc cga -3'
Primer lacΔ(−):
5'P- TCG GGG CTG GCT TAA ACT cat cag gcg cca ttc -3'

These primers are complementary to sequences in the plasmid pUC19 flanking the lacZ' sequence that is substituted in Example 3. In fact, they have the same pUC19 sequences as the PCR generated insertion primers in Example 3, except that the sequence of bleomycin resistance gene is replaced by the termination codon TAG. This TAG sequence is artificially introduced to terminate lacZ' protein translation at the deletion site so the activity of the deleted lacZ' protein can be studied. Depending on specific application, any or no artificial sequences may be introduced at the deletion site using this method.

This deletion process is schematically illustrated in FIG. 4. As illustrated in FIG. 4, the thick line represents the sequence to be deleted. The black and gray lines represent sequences of the inner and outer strands respectively. The deletion primers are shown as tailed arrows, their heads (3') and tails (5') are complementary to the sequences flanking the region to be deleted. Dashed lines indicate the newly synthesized strand. Target DNA, deletion primers, thermostable DNA polymerase, ligase, dNTPs, and buffer are mixed; and the mixture is subjected to thermocycling of 95° C. to 50° C. to 72° C. DNA is denatured at 95° C., the deletion primers anneal to the target DNA at 50° C. via their 3' and 5' complementary ends to bring together the two deletion ends and form a loop in the target DNA. The loop contains the to-be deleted sequence. The polymerase extends the primers at 72° C. thereby copying the remaining sequence of the target DNA. The nicks are then closed by the ligase and form the deleted recombinant. During subsequent thermocycles, the deletion primers will exponentially amplify the closed circular recombinant DNA. As shown, the target sequence (thick line) has been deleted in the resulting recombinant DNA. The detailed cloning procedures and conditions are the same as described in Example 1.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

We claim:

1. A method for in vitro automated molecular cloning and amplification of a closed circular nucleic acid in a single reaction container, comprising:
   (a) mixing an effective amount of a donor nucleic acid comprising the donor sequence to be cloned, a recipient closed circular nucleic acid, a pair of 5'-phosphorylated cloning primers having the 3' and 5' portions complementary to different strands of the donor and recipient sequence, a thermostable DNA ligase, a thermostable DNA polymerase, all four deoxyribonucleoside triphosphates, and an appropriate buffer comprising all cofactors required for activity of both the ligase and polymerase in a single suitable reaction tube to form an automated in vitro cloning mixture which produces amplified closed circular recombinant clones; and
   (b) subjecting the cloning mixture tube to a single ligation during amplification (LDA) reaction process comprising a selected number of PCR cycles at a suitable denaturing temperature, then a suitable annealing temperature, and then a suitable extension temperature thereby forming a pair of insertion primers containing the donor nucleic acid to be inserted and causing said insertion primers to be extended by the polymerase, then ligated by the ligase for closing the extended insertion primers and then amplified exponentially to form closed circular nucleic acid recombinant clones containing the donor nucleic acid being inserted in the recipient closed circular nucleic acid in an inverted orientation.

2. The method of claim 1, wherein said donor nucleic acid, closed circular recipient nucleic acid, and closed circular nucleic acid recombinant clone is DNA.

3. The method of claim 1 wherein the cloning mixture is held in each cycle at the denaturing temperature for 1 second to 2 minutes, at the annealing temperature for 1 second to 5 minutes and at the extension temperature for 1 to 20 minutes.

4. The method of claim 1 wherein said closed circular recipient nucleic acid is replicatively competent.

5. The method of claim 1 wherein said donor nucleic acid is RNA and said thermostable DNA polymerase is a reverse transcriptase.

6. A method for in vitro automated molecular cloning and amplification of a closed circular nucleic acid in a single reaction container, comprising:

(a) mixing an effective amount of a donor nucleic acid comprising the donor sequence to be cloned, a recipient closed circular nucleic acid, a pair of 5'-phosphorylated cloning primers having the 3' and 5' portions complementary to the same strands of the donor and recipient sequence, a thermostable DNA ligase, a thermostable DNA polymerase, all four deoxyribonucleoside triphosphates, and an appropriate buffer comprising all cofactors required for activity of both the ligase and polymerase in a single suitable reaction tube to form an automated in vitro cloning mixture which produces amplified closed circular recombinant clones; and (b) subjecting the cloning mixture tube to a single ligation during amplification (LDA) reaction process comprising a selected number of PCR cycles at a suitable denaturing temperature, then a suitable annealing temperature, and then a suitable extension temperature; thereby forming a pair of insertion primers containing the donor nucleic acid to be inserted, and causing said insertion primers to be extended by the polymerase then ligated by the ligase for closing the extended insertion primers and then amplified exponentially to form closed circular nucleic acid recombinant clones containing the donor nucleic acid being inserted in the recipient closed circular nucleic acid in a non-inverted orientation.

7. The method of claim 6 wherein said donor nucleic acid, closed circular recipient nucleic acid, and closed circular nucleic acid recombinant clone is DNA.

8. The method of claim 6 wherein the cloning mixture is held in each cycle at the denaturing temperature for 1 second to 2 minutes, at the annealing temperature for 1 second to 5 minutes and at the extension temperature for 1 to 20 minutes.

9. The method of claim 6 wherein said closed circular recipient nucleic acid is replicatively competent.

10. The method of claim 6 wherein said donor nucleic acid is RNA and said thermostable DNA polymerase is a reverse transcriptase.

11. A method for in vitro automated molecular cloning and amplification of a closed circular nucleic acid in a single reaction container, comprising:

(a) mixing an effective amount of a donor nucleic acid comprising the donor sequence to be cloned, a recipient closed circular nucleic acid, a pair of 5'-phosphorylated cloning primers having 3' portions complementary to the donor sequence and 5' portions complementary to sequences flanking a region to be substituted on the recipient sequence, a thermostable DNA ligase, a thermostable DNA polymerase, all four deoxyribonucleoside triphosphates, and an appropriate buffer comprising all cofactors required for activity of both the ligase and polymerase in a single suitable reaction tube to form an automated in vitro cloning mixture which produces amplified closed circular recombinant clones; and (b) subjecting the cloning mixture tube to a single ligation during amplification (LDA) reaction process comprising a selected number of PCR cycles at a suitable denaturing temperature, then a suitable annealing temperature, and then a suitable extension temperature; thereby forming a pair of insertion primers containing the donor nucleic acid to be inserted, and causing said insertion primers to be extended by the polymerase, then ligated by the ligase for closing the extended insertion primers and amplified exponentially to form closed circular nucleic acid recombinant clones wherein the recipient sequence being substituted by the donor sequence.

12. The method of claim 11 wherein said donor nucleic acid, closed circular recipient nucleic acid, and closed circular nucleic acid recombinant clone is DNA.

13. The method of claim 11 wherein the cloning mixture is held in each cycle at the denaturing temperature for 1 second to 2 minutes, at the annealing temperature for 1 second to 5 minutes and at the extension temperature for 1 to 20 minutes.

14. The method of claim 11 wherein said closed circular recipient nucleic acid is replicatively competent.

15. The method of claim 1 wherein said donor nucleic acid is RNA and said thermostable DNA polymerase is a reverse transcriptase.

16. A method for in vitro automated molecular cloning and amplification of a closed circular nucleic acid in a single reaction container, comprising:

(a) mixing an effective amount of a recipient closed circular nucleic acid containing a sequence to be deleted, a pair of 5'-phosphorylated cloning primers complementary to sequences flanking the region to be deleted on the recipient sequence, a thermostable DNA ligase, a thermostable DNA polymerase, all four deoxyribonucleoside triphosphates, and an appropriate buffer comprising all cofactors required for activity of both the ligase and polymerase in a single suitable reaction tube to form an automated in vitro cloning mixture which produces amplified closed circular recombinant clones; and (b) subjecting the cloning mixture tube to a single ligation during amplification (LDA) reaction process comprising a selected number of PCR cycles at a suitable denaturing temperature, then a suitable annealing temperature, and then a suitable extension temperature; thereby causing said cloning primers to be extended by the polymerase, ligated by the ligase for closing the extended insertion primers and amplified exponentially to form closed circular nucleic acid recombinant clones with a deleted sequence.

17. The method of claim 16 wherein said closed circular recipient nucleic acid, and closed circular nucleic acid recombinant clone is DNA.

18. The method of claim 16 wherein the cloning mixture is held in each cycle at the denaturing temperature for 1 second to 2 minutes, at the annealing temperature for 1 second to 5 minutes and at the extension temperature for 1 to 20 minutes.

19. The method of claim 16 wherein said closed circular recipient nucleic acid is replicatively competent.

20. The method of claim 16 wherein said donor nucleic acid is RNA and said thermostable DNA polymerase is a reverse transcriptase.

* * * * *